US011684907B2

(12) United States Patent
Park et al.

(10) Patent No.: US 11,684,907 B2
(45) Date of Patent: Jun. 27, 2023

(54) CATALYST HAVING ENHANCED CONVERSION AND SELECTIVITY FOR MANUFACTURING OLEFIN, AND MANUFACTURING METHOD THEROF

(71) Applicants: SK GAS CO., LTD., Seongnam-si (KR); KOREA RESEARCH INSTITUTE OF CHEMICAL TECHNOLOGY, Daejeon (KR)

(72) Inventors: Yong Ki Park, Seoul (KR); Won Choon Choi, Daejeon (KR); Daesung Park, Daejeon (KR); Hawon Park, Daejeon (KR); Deuk Soo Park, Yongin-si (KR); Ung Gi Hong, Seongnam-si (KR); Byungjun Kang, Seongnam-si (KR); Miyoung Lee, Seoul (KR)

(73) Assignees: SK GAS CO., LTD., Seongnam-si (KR); KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 298 days.

(21) Appl. No.: 17/253,835

(22) PCT Filed: Apr. 15, 2019

(86) PCT No.: PCT/KR2019/004511
§ 371 (c)(1),
(2) Date: Dec. 18, 2020

(87) PCT Pub. No.: WO2020/009318
PCT Pub. Date: Jan. 9, 2020

(65) Prior Publication Data
US 2021/0113993 A1    Apr. 22, 2021

(30) Foreign Application Priority Data
Jul. 4, 2018    (KR) .................. 10-2018-0077399

(51) Int. Cl.
*B01J 23/30*    (2006.01)
*B01J 21/06*    (2006.01)
*B01J 23/26*    (2006.01)
*B01J 37/02*    (2006.01)
*B01J 37/08*    (2006.01)
*C07C 5/333*    (2006.01)

(52) U.S. Cl.
CPC ............. *B01J 23/30* (2013.01); *B01J 21/066* (2013.01); *B01J 23/26* (2013.01); *B01J 37/024* (2013.01); *B01J 37/0205* (2013.01); *B01J 37/0236* (2013.01); *B01J 37/08* (2013.01); *C07C 5/3332* (2013.01); *C07C 2521/06* (2013.01); *C07C 2523/26* (2013.01); *C07C 2523/30* (2013.01)

(58) Field of Classification Search
CPC . B01J 23/30; B01J 23/26; B01J 21/066; B01J 37/0205; B01J 37/0236; B01J 37/024; B01J 37/08; C07C 5/3332
See application file for complete search history.

(56) References Cited

FOREIGN PATENT DOCUMENTS

JP          2014-534902 A    12/2014
KR    10-2012-0077688 A     7/2012

OTHER PUBLICATIONS

Sim et al., Molecular Catalysis, (2017), v.436, p. 164-173.*
Liu et al., Chem. Lett., (1998), p. 1057-1058.*
Zhu et al., Catal. Today, (2009), v.148, p. 310-315.*
International Search Report for PCT/KR2019/004511 dated Jul. 24, 2019 from Korean Intellectual Property Office.
Shim, Seohyeon, "A study of Zr modification for improvements in durability and selectivity of $CrO_x/Al_2O_3$ catalyst during PDH reaction", Master's Thesis, The University of Science and Technology, Aug. 2017, pp. 1-67.
Jianqiang Zhu et al., "$Na_2WO_4/Mn/SiO_2$ catalyst for oxidative dehydrogenation of ethane using $CO_2$ as oxidant", Catalysis Today, Aug. 13, 2009, pp. 310-315, vol. No. 148.
Seohyun Sim et al., "Chromium oxide supported on Zr modified alumina for stable and selective propane dehydrogenation in oxygen free moving bed process", Molecular Catalysis, May 1, 2017, pp. 164-173, vol. No. 436.

* cited by examiner

*Primary Examiner* — Yong L Chu
(74) *Attorney, Agent, or Firm* — Paratus Law Group, PLLC

(57) ABSTRACT

Disclosed is a catalyst for producing an olefin, the catalyst having an excellent conversion and excellent selectivity, and a method for preparing the catalyst. The catalyst for producing an olefin, according to the present invention, includes: a support including alumina and an auxiliary support component; a main catalyst including an active metal oxide supported on the support; and a co-catalyst including an oxide of an alkali metal and a Group 6B transition metal.

6 Claims, 2 Drawing Sheets

CATALYST HAVING ENHANCED CONVERSION AND SELECTIVITY FOR MANUFACTURING OLEFIN, AND MANUFACTURING METHOD THEROF

CROSS-REFERENCE TO PRIOR APPLICATIONS

This application is a National Stage Patent Application of PCT International Patent Application No. PCT/KR2019/004511 (filed on Apr. 15, 2019) under 35 U.S.C. § 371, which claims priority to Korean Patent Application No. 10-2018-0077399 (filed on Jul. 4, 2018), which are all hereby incorporated by reference in their entirety.

BACKGROUND

The present invention relates to a catalyst for producing an olefin, the catalyst having an excellent conversion and excellent selectivity compared to those in the related art, and a method for preparing the same.

Olefins such as ethylene and propylene have been widely used in the petrochemical industry. In general, these olefins are obtained by a pyrolysis process of naphtha. However, since the petrochemical industry requires larger amounts of olefins, olefins are also produced via a dehydrogenation process using lower hydrocarbon catalysts.

All existing propane dehydrogenation (PDH) commercial processes use fixed bed reactors.

In contrast, fast-fluidized propane dehydrogenation (FPDH) using a fluidized bed reactor has not been commercialized to date.

The biggest difference between the fixed bed reactor and the fluidized bed reactor is the contact time between a catalyst and a reactant (propane). That is, the FPDH is a process in which propane and a catalyst are injected together into a fluidized bed reactor at a very high rate to react the propane and the catalyst, and then the catalyst enters a regeneration part and a product enters a separation part.

A goal of a conventionally developed FPDH process is to reduce the residence time of a catalyst to 10 seconds or less. Since the residence time of the catalyst is short, the injection rate of the amount of propane supply is correspondingly fast, and the catalyst is immediately regenerated and participates in the reaction again, the amount of propylene produced when the FPDH process is developed as a commercial process is increased significantly compared to the fixed bed process.

However, the efficiency of the catalyst becomes very important because the contact time between the catalyst and propane is so short. That is, it is important to maximize the selectivity and conversion, which are two measures of the efficiency of the catalyst.

Furthermore, the propane dehydrogenation process technologies currently used are constituted based on a noble metal catalyst or a discontinuous process, and there is a problem with the operation of a catalyst bed even in a continuous process, so that the technologies are not suitable for mass production of propylene on the scale of several million tons. Further, the propane dehydrogenation reaction has a thermodynamic limitation on the propane conversion due to the reversible reaction between propylene and hydrogen, which are produced. Accordingly, in order to effectively mass-produce propylene, there is a need for developing a new propane dehydrogenation process with reduced production costs by solving the problems of the continuous process and using an inexpensive non-noble metal catalyst in which the selectivity and the conversion are maximized.

In the case of a noble metal catalyst among catalysts used for propane dehydrogenation, the reaction proceeds by a direct dehydrogenation mechanism in which hydrogen is adsorbed on an active site, but in the case of transition metal oxides, the mechanism has not been clearly elucidated due to the incompleteness of the active site caused by electron mobility.

Under these circumstances, the catalysts most commonly used as PDH catalysts are Pt, Pt—Sn, VOx, and CrOx catalysts, and the CrOx catalyst is extremely excellent in terms of propane conversion and selectivity. However, platinum catalysts have excellent selectivity, but have the disadvantages of a high price and a very low conversion.

A CrOx catalyst, which is a representative oxide catalyst, is a form in which $Cr^{6+}$ and $Cr^{3+}$ are stable, and most of the catalyst prepared by calcining at a high temperature is in the $Cr^{3+}$ state as $Cr_2O_3$, but some $Cr^{6+}$ is present. In the catalyst thus prepared (new catalyst), the oxygen (generated from the lattice oxygen of the oxidation catalyst) generated while $Cr^{6+}$ is reduced to $Cr^{3+}$ at the initial stage of the reaction participates in the propane dehydrogenation reaction, thereby contributing to the production of $CO_2$ rather than propylene.

In the fixed bed reactor, an increase in the residence time of the catalyst does not make a big problem in the initial $CO_2$ selectivity (high selectivity propylene is produced even a few seconds after the reaction).

However, since the residence time of the catalyst in the fluidized bed reactor is within 10 seconds, $CO_2$ production by the complete oxidation reaction of propane on a transition metal oxide catalyst becomes a big problem at the initial stage of the reaction, so that it is essential to control the level of oxidation of the transition metal in order to secure propylene selectivity. After all, in the case of the FPDH process using a fluidized bed reactor, the selectivity issue is very important because the reaction time is short.

Thus, the present inventors have discovered through continuous studies that problems in the related art can be solved by introducing a co-catalyst, thereby developing a catalyst for producing an olefin, the catalyst having an excellent conversion and excellent selectivity, and a method for preparing the same.

SUMMARY

An object of the present invention is to provide a catalyst for producing an olefin, the catalyst having an excellent conversion and excellent selectivity, and a method for preparing the catalyst.

It is preferred that the catalyst for producing an olefin, according to the present invention, includes: a support including alumina and an auxiliary support component; and a main catalyst including an active metal oxide supported on the support; and includes or does not include a co-catalyst including an oxide of an alkali metal and a Group 6B transition metal.

It is preferred that the auxiliary support component includes one or more selected from zirconium and phosphorus (P).

As the auxiliary support component, zirconium is particularly preferred, and it is preferred that the zirconium is present at a molar fraction of 0.01 to 0.1 (Zr:Al) with respect to aluminum in alumina.

It is preferred that the active metal component includes one or more selected from oxides of chromium, vanadium, manganese, iron, cobalt, molybdenum, copper, zinc, cerium, and nickel.

As the active metal component, chromium is particularly preferred, and it is preferred that the active metal component is included in an amount of 1 to 20 wt % in the catalyst.

It is more preferred that the alkali metal is sodium.

It is more preferred that the Group 6B transition metal is tungsten.

It is preferred that the co-catalyst is included in an amount of 0.01 wt % or more and less than 1 wt %.

It is preferred that the method for producing an olefin, according to the present invention, includes: providing a support including an auxiliary support component and alumina;

impregnating a main catalyst including an active metal oxide on the support; and drying and calcining the support in which the main catalyst is supported, in which when the co-catalyst is additionally supported, a co-catalyst including an oxide of an alkali metal and a Group 6B transition metal is simultaneously mixed with the support; or is impregnated immediately after the drying step, and dried and calcined; or impregnated immediately after the calcination step, and dried and calcined.

It is preferred that the auxiliary support component includes one or more selected from zirconium and phosphorus (P).

As the auxiliary support component, zirconium is particularly preferred, and it is preferred that the zirconium is present at a molar fraction of 0.01 to 0.1 (Zr:Al) with respect to aluminum in alumina.

It is preferred that the active metal component includes one or more selected from oxides of chromium, vanadium, manganese, iron, cobalt, molybdenum, copper, zinc, cerium, and nickel.

As the active metal component, chromium is particularly preferred, and it is preferred that the active metal component is included in an amount of 1 to 20 wt % in the catalyst.

It is more preferred that the alkali metal is sodium.

It is more preferred that the Group 6B transition metal is tungsten.

It is preferred that the co-catalyst is included in an amount of 0.01 wt % or more and less than 1 wt %.

It is preferred that the drying step is performed at 100° C. to 150° C.

It is preferred that the calcination step is performed at 700° C. to 850° C.

The catalyst for producing an olefin and the method for preparing the same, according to the present invention, have an excellent conversion and excellent selectivity, and thus are effective for both a fixed bed reactor and a fluidized bed reactor, but particularly enables the realization of an FPDH process which has not been commercially implemented in the related art.

DETAILED DESCRIPTION

Figure 1:
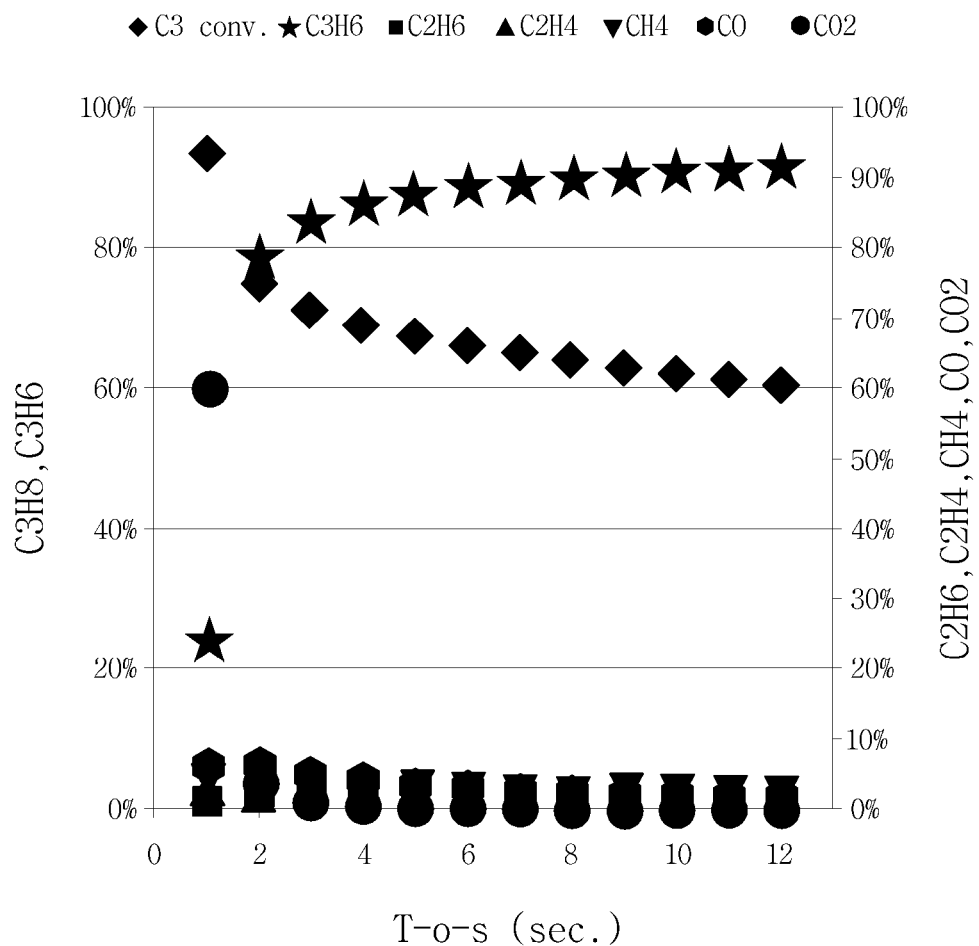
FIG. 1 schematically illustrates the activity of a catalyst which does not include a co-catalyst according to the present invention.

It is preferred that the catalyst for producing an olefin, according to the present invention, includes a support including alumina and an auxiliary support component and a main catalyst including an active metal oxide supported on the support; and includes or does not include a co-catalyst including an oxide of an alkali metal and a Group 6B transition metal.

It is preferred that the method for producing an olefin, according to the present invention, includes: providing a support including an auxiliary support component and alumina;

supporting a main catalyst including an active metal oxide; and drying and calcining the support in which the main catalyst is supported, in which when the co-catalyst is additionally supported, a co-catalyst including an oxide of an alkali metal and a Group 6B transition metal is simultaneously mixed with the support; or is impregnated immediately after the drying step, and dried and calcined; or impregnated immediately after the calcination step, and dried and calcined.

Hereinafter, preferred exemplary embodiments of the present invention will be described with reference to the accompanying drawings. However, the exemplary embodiments of the present invention may be modified into various other forms, and the scope of the present invention is not limited to the exemplary embodiments which will be described below.

In describing these examples, the same names and symbols are used for the same configuration, and accordingly, the overlapping additional description will be omitted below. A scale ratio does not apply in the drawings referenced below, and the percentage (%) used in the description of the present invention, such as in the examples and drawings below, means a weight ratio (wt %) unless otherwise defined.

It is preferred that the catalyst for producing an olefin, according to the present invention, includes a support including alumina and an auxiliary support component and a main catalyst including an active metal oxide supported on the support; and includes or does not include a co-catalyst including an oxide of an alkali metal and a Group 6B transition metal.

It is preferred that the auxiliary support component includes one or more selected from zirconium and phosphorus (P).

As the auxiliary support component, zirconium is particularly preferred, and it is preferred that the zirconium is present at a molar fraction of 0.01 to 0.1 (Zr:Al) with respect to aluminum in alumina.

The catalyst according to the present invention has improved durability due to the auxiliary support component, and a superior function of exciting the C—H bond of a paraffin raw material compared to the case where only alumina is used as the support. Thereby the hydrocarbon conversion and the olefin yield are excellent, and olefin selectivity is also improved. In particular, zirconium serves to improve the durability of an alumina support.

When the content of the auxiliary support component, particularly zirconium, is less than a molar ratio of 0.01 with respect to aluminum, the durability improvement effect feature does not appear, and when the content exceeds a molar ratio of 0.1, the surface area of the alumina support is sharply reduced, so that the active metal component supported cannot be polydispersed.

It is preferred that the active metal component includes one or more selected from oxides of chromium, vanadium, manganese, iron, cobalt, molybdenum, copper, zinc, cerium, and nickel.

As the active metal component, chromium is particularly preferred, and it is preferred that the active metal component is included in an amount of 1 to 20 wt % in the catalyst.

When the content of the active metal component exceeds 20 wt %, the main active phase in chromium may be decreased by the metal-support interaction and an excessive metal bonding force, which is not preferred. The alumina support preferably has a γ to θ phase at a preparation temperature of 550 to 850° C., which is equal to or higher than the dehydrogenation reaction temperature, and has a surface area of 80 to 300 m²/g in this range.

When the support is prepared at a temperature lower than the dehydrogenation reaction temperature, thermal transformation of the catalyst may occur during the dehydrogenation reaction, and when the support is prepared at a temperature higher than 850° C., crystallization of the support results in a low catalyst surface area, which will interfere with the transfer of material for catalytic activity upon contact with the reactants.

It is more preferred that the alkali metal is sodium.

It is more preferred that the Group 6B transition metal is tungsten.

It is preferred that the co-catalyst is included in an amount of 0.01 wt % or more and less than 1 wt %. When the amount of the co-catalyst is less than 0.01 wt %, the effect of increasing the propylene selectivity of the active metal catalyst is insignificant, and when the amount is more than 1 wt %, the conversion of propane is sharply decreased.

It is preferred that the method for producing an olefin, according to the present invention, includes: providing a support including an auxiliary support component and alumina;

supporting a main catalyst including an active metal and an auxiliary active metal oxide on the support; and drying and calcining the support in which the main catalyst is supported, in which when the co-catalyst is additionally supported, a co-catalyst including an oxide of an alkali metal and a Group 6B transition metal is simultaneously mixed with the support; or is impregnated immediately after the drying step, and dried and calcined; or impregnated immediately after the calcination step, and dried and calcined.

It is preferred that the drying step is performed at 100° C. to 150° C.

It is preferred that the calcination step is performed at 700° C. to 850° C.

In spite of the above preparation method, it will be obvious to those skilled in the art that various preparation methods are possible within a scope not departing from the scope of the present invention.

Hereinafter, the present invention will be described in more detail through Preparation Examples and Examples.

PREPARATION EXAMPLES

1. Preparation of Support (Zr—Al₂O₃)

After 25 kg of water was added to 13.89 kg of Catapal B (alumina, sold by Sasol) and the resulting mixture was stirred for 30 minutes, 1.83 kg of $ZrO(NO_3)_2$ and 25 kg of water were mixed therewith, and the resulting mixture was stirred for an additional 2.5 hours. After spray drying (feed rate 0.56 g/min, atomizer 6000 rpm, inlet temperature 208° C., outlet temperature 125° C.), sieving (75 to 200 μm) was performed, and the product was calcined at 650° C. for 6 hours.

2. Preparation of Catalyst [(1 to 15% Cr+0.1 to 1% Na₂WO₄)/Zr—Al₂O₃]

Based on 10 g of the support (Zr—Al₂O₃) prepared in Preparation Example 1, 0.19 to 3.39 g (1 to 15 wt % based on Cr) of CrO₃ (chromium trioxide, 99.9%) and 0.072 to 0.725 g (0.1 to 1 wt % based on Na) of Na₂WO₄ (sodium tungstate, dihydrate) were mixed with 5 g of water, and the resulting mixture was stirred for 1 hour. After a mixture of chromium and a Na₂WO₄ precursor was impregnated in 10 g of a support and dried at 120° C., a catalyst of the present invention was prepared by calcining the resulting product at 850° C. for 10 hours.

<Conversion and Selectivity Experiments>

In order to confirm the conversion and selectivity of the catalyst prepared by the present invention, a GC (FID, TCD) analysis was performed in a fixed bed quartz downflow reactor in which the catalyst was maintained at WHSV=2.0 to 17.3 h⁻¹ at 550 to 640° C. and atmospheric pressure.

The experimental results in which the co-catalyst was not included are illustrated in FIG. 1. As illustrated in FIG. 1, the yield of propylene was very excellent even when the co-catalyst was not included according to the present invention.

Figure 2:
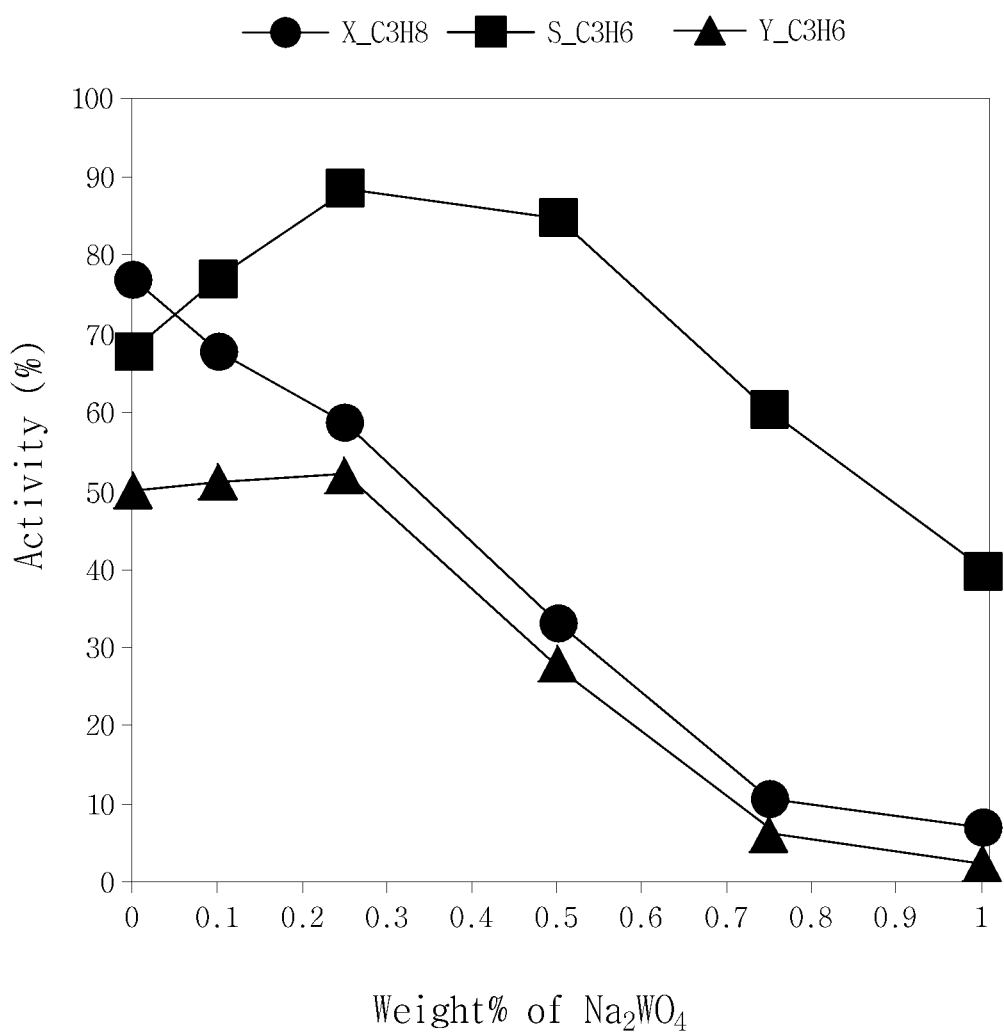
FIG. 2 schematically illustrates the activity of a catalyst including a co-catalyst according to the present invention.

Meanwhile, experimental results (initial 1 to 4 second intervals) in which the co-catalyst was included according to the present invention are illustrated in the following Table 1 and FIG. 2. The selectivity and conversion when the co-catalyst was included were better than those when the co-catalyst was not included.

TABLE 1

| Na₂WO₄, wt % | | 0 | 0.1 | 0.25 | 0.5 | 0.75 | 1.0 |
|---|---|---|---|---|---|---|---|
| Propane conversion (wt %) | | 77.2 | 67.7 | 58.8 | 33.3 | 10.8 | 6.9 |
| Selectivity (wt %) | Propylene | 67.9 | 77.0 | 88.6 | 84.9 | 60.3 | 39.8 |
| | CO₂ | 16.6 | 7.9 | 1.4 | 4.0 | 7.3 | 14.1 |
| Yield (wt %) | Propylene | 50.0 | 51.1 | 52.0 | 27.8 | 6.3 | 2.5 |

Even though the exemplary embodiments of the present invention have been described in detail, the scope of rights of the present invention is not limited thereto, and it will be obvious to a person with ordinary skill in the art that various modifications and alterations are possible without departing from the technical spirit of the present invention described in the claims.

The present invention provides a catalyst for producing an olefin, the catalyst having an excellent conversion and excellent selectivity, and a method for preparing the same.

The invention claimed is:

1. A catalyst for producing an olefin by direct dehydrogenation, the catalyst comprising: a support comprising alumina and an auxiliary support component; and a main catalyst comprising an active metal oxide supported on the support; and the catalyst comprising 0.01 wt % or more and less than 1 wt % of a co-catalyst comprising an oxide of an alkali metal and a Group 6B transition metal, wherein the catalyst is configured to produce an olefin by direct dehydrogenation wherein the alkali metal is sodium, and wherein the Group 6B transition metal is tungsten.

2. The catalyst of claim 1, wherein the auxiliary support component comprises one or more selected from zirconium and phosphorus (P).

3. The catalyst of claim 1, wherein the auxiliary support component is zirconium, and the zirconium is present at a molar fraction of 0.01 to 0.1 (Zr:Al) with respect to aluminum in the alumina.

4. The catalyst of claim 1, wherein the active metal oxide comprises one or more selected from oxides of chromium, vanadium, manganese, iron, cobalt, molybdenum, copper, zinc, cerium, and nickel.

5. The catalyst of claim 1, wherein the active metal oxide is chromium oxide, and is comprised in an amount of 1 to 20 wt %.

6. The catalyst of claim 1, wherein the catalyst is made by a method comprising:
   providing the support comprising the auxiliary support component and alumina;
   impregnating the main catalyst comprising an active metal oxide on the support;
   drying the support on which the main catalyst is supported; and
   calcining the support in which the main catalyst is supported,
   simultaneously mixing the co-catalyst comprising an oxide of an alkali metal and a Group 6B transition metal with the support prior to the steps of drying and calcining; or alternatively impregnating the support with the co-catalyst immediately after drying; or impregnating the support with the co-catalyst immediately after the calcination step; or impregnating the support with the co-catalyst immediately after the steps of drying and calcining,
   wherein the co-catalyst is contained in the catalyst of claim 1 in an amount of 0.01% by weight or more and less than 1% by weight.

\* \* \* \* \*